(12) United States Patent
Lawrence et al.

(10) Patent No.: US 7,435,577 B2
(45) Date of Patent: Oct. 14, 2008

(54) DIRECT MEASUREMENT OF CHLOLESTEROL FROM LOW DENSITY LIPOPROTEIN WITH TEST STRIP

(75) Inventors: Gregory M. Lawrence, Indianapolis, IN (US); John Pasqua, Indianapolis, IN (US)

(73) Assignee: Polymer Technology Systems, Inc., Indianapolis, IN (US)

( * ) Notice: Subject to any disclaimer, the term of this patent is extended or adjusted under 35 U.S.C. 154(b) by 345 days.

(21) Appl. No.: 10/962,272

(22) Filed: Oct. 11, 2004

(65) Prior Publication Data

US 2005/0170447 A1 Aug. 4, 2005

Related U.S. Application Data

(60) Provisional application No. 60/541,681, filed on Feb. 3, 2004.

(51) Int. Cl.
*C12M 1/34* (2006.01)
*C12M 3/00* (2006.01)

(52) U.S. Cl. .................................. 435/287.7

(58) Field of Classification Search ........ None
See application file for complete search history.

(56) References Cited

U.S. PATENT DOCUMENTS

| | | | |
|---|---|---|---|
| 3,809,617 A | 5/1974 | Schmitt | |
| 4,178,153 A | 12/1979 | Sodickson | |
| 4,477,575 A | 10/1984 | Vogel et al. | |
| 4,738,823 A | 4/1988 | Engelmann | |
| 4,774,192 A | 9/1988 | Terminiello et al. | |
| 5,135,716 A | 8/1992 | Thakore | |
| 5,597,532 A | 1/1997 | Connolly | |
| 5,888,827 A | 3/1999 | Kayahara et al. | |
| 6,063,337 A | 5/2000 | Markart | |
| 6,171,849 B1 | 1/2001 | Rittersdorf et al. | |
| 6,194,164 B1 | 2/2001 | Matsui et al. | |
| 6,342,364 B1 | 1/2002 | Watanabe et al. | |
| 6,759,190 B2 | 7/2004 | Lin et al. | |
| 2003/0003522 A1 | 1/2003 | Goldman | |
| 2003/0092102 A1 | 5/2003 | Rosen et al. | |
| 2003/0166291 A1 | 9/2003 | Jones et al. | |
| 2004/0126830 A1 | 7/2004 | Shull et al. | |
| 2005/0003523 A1 | 1/2005 | Anaokar et al. | |
| 2005/0170447 A1 | 8/2005 | Lawrence et al. | |

FOREIGN PATENT DOCUMENTS

| | | |
|---|---|---|
| DE | 3217925 A1 | 11/1983 |
| DE | 3401932 A1 | 8/1985 |
| DE | 19942928 A1 | 4/2001 |
| EP | 0260965 A | 3/1988 |
| EP | 0269876 A | 6/1988 |
| EP | 0389003 A | 9/1990 |
| EP | 0418169 A | 3/1991 |
| EP | 0511120 A | 10/1992 |
| EP | 0597268 A | 5/1994 |
| EP | 0753583 A | 1/1997 |
| JP | 02064455 | 3/1990 |
| WO | WO-00/73797 A | 12/2000 |
| WO | WO-03/025574 A | 3/2003 |

OTHER PUBLICATIONS

Santee Am J Health-Syst Pharm 2002;59:1774-1779.*
Feng et al. "Adsorption of high density lipoproteins (HDL) on solid surfaces" J of colloid and interface science, 1996, 177:364-371.*
Warnick et al., "Evolution methods for measurement of HDL-cholesterol: from ultracentrifugation to homogeneous assays", Clinical Chemistry, vol. 47, No. 9, 2001, pp. 1579-1596.
Nauck et al., "Methods of measurement of LDL-cholesterol: a critical assessment of direct measurement by homogeneous assays versus calculation", Clinical Chemistry, vol. 48, No. 2, 2002, pp. 236-254.

* cited by examiner

*Primary Examiner*—Jon P Weber
*Assistant Examiner*—Bin Shen
(74) *Attorney, Agent, or Firm*—Patton Boggs LLP

(57) ABSTRACT

Cholesterol from Low Density Lipoproteins (LDL-C) is measured directly with a test strip at room temperature using a reagent that takes advantage of the varying surface charge density on LDLs and non-LDLs to selectively make LDL-C available for testing.

18 Claims, 9 Drawing Sheets

US 7,435,577 B2

DIRECT MEASUREMENT OF CHLOLESTEROL FROM LOW DENSITY LIPOPROTEIN WITH TEST STRIP

BACKGROUND OF THE INVENTION

This invention relates generally to the in vitro analysis, using a dry test strip, of plasma, serum or whole blood samples, and more specifically, to assay for cholesterol from Low Density Lipoproteins (LDL-C) contained in samples.

The level of cholesterol in blood has become accepted as a significant indicator of risk of coronary heart disease. Cholesterol is contained and is transported in lipoproteins in blood. "Total Cholesterol" includes cholesterol from Low Density Lipoproteins (LDL-C), from Intermediate Density Lipoproteins (IDL-C), from Chylomicrons, from Very Low Density Lipoproteins (VLDL-C) and from high density lipoproteins (HDL-C). It is well established from epidemiological and clinical studies that there is a positive correlation between levels of LDL-C and to a lesser extent of Lp(a)-C to coronary heart disease. Traditionally, LDL-C has been identified as "bad" cholesterol. On the other hand, clinical studies have established a negative correlation between levels of HLD-C ("good" cholesterol) and coronary heart disease. Standing alone, the level of total cholesterol in blood, which is a measure of the sum total of HDL-C, LDL-C, IDL-C, VLDL-C and Chylomicrons-C, is not generally regarded as an adequate indicator of the risk of coronary heart disease because the overall level of total cholesterol does not reveal the relative proportions of cholesterol from these sources. To better assess the risk of heart disease, it is desirable to determine the amount of LDL-C in a sample in addition to the total cholesterol in the sample.

The most common approach to determining LDL-C in the clinical laboratory is the Friedewald calculation, which estimates LDL-C from measurements of total cholesterol, HDL-C and triglycerides. Although convenient, the Friedewald calculation suffers from several well-established drawbacks. Nauck et al. "Methods of Measurement of LDL-Cholesterol: A critical Assessment of Direct Measurement by Homogeneous Assays versus Calculation" Clin. Chem. 48.2 (2002). For example, because the Friedewald calculation involves measurother than LDL-C, it is subject to potential compounded inaccuracies from the determinations of the other lipids in the equation. Further, its usefulness is known to be limited to biological fluids with trigylceride levels below 400 mg/d L, and its accuracy reportedly declines with triglyceride levels greater than 200 mg/dL.

Ultra-centrifugation is a known technique to separate and to quantify the various lipoprotein components from serum or plasma samples. However, ultra-centrifugation is tedious, time consuming, and the highly labile lipoproteins can be substantially altered by the high salt concentrations that are a part of the ultra-centrifugation process as well as by centrifugal forces. "Furthermore, a plethora of different types of equipment and tubes are used, making conditions difficult to reproduce from one laboratory to another and consistent separations highly dependent on the skills and care of the technician." Id. At 238.

Another technique for measuring LDL-C is electrophoresis. This technique also has certain drawbacks. Electrophoresis gel assays do not lend themselves readily to automation and their accuracy and repeatability depends at least in part on the technique of the technician performing the test.

Other so-called homogeneous methods that involve precipitation of non-LDL lipoproteins, heating and additional steps, have recently become available. One homogeneous method for determining LDL-C is disclosed in U.S. Pat. No. 5,888,827 (Kayahara, Sugiuchi, et al.; assigned to Kyowa Medex Co., Japan). The '827 patent describes a two-stage liquid phase reaction to quantify LDL-C concentration in a fluid sample. In the first step, the sample containing LDL-C is placed in a first reagent that includes trimethyl beta-cyclodextrin as a sugar compound, polyoxyethylene monolaurate as a protein solubilizing agent, EMSE (N-ethyl-N-(3-methylphenyl)-N',succinylethylenediamene) and Tris buffer. The reaction mixture is then heated to 37° C., and after 5 minutes the absorbance is read. A second reagent including cholesterol esterase, cholesterol oxidase, peroxidase, 4-aminoantipyrine and Tris buffer is then added and after another 5 minutes the absorbance is again measured at the same wavelength. LDL-C is then calculated by separately subjecting a standard solution of cholesterol to the same procedure and comparing the respective absorbance values. For many applications the manipulations required in the practice of this method such as heating, multiple reagents and multiple readings is considered a drawback. Because this method is complex and tedious to perform even in a laboratory, it would not be suitable for a point-of-care (POC) environment.

Another two-stage homoegneous assay is disclosed in U.S. Pat. No. 6,194,164 (Matsui et al.; assigned to Denke Seiken, Ltd. Japan). In the first stage, HDL-C, VLDL-C and Chylomicron-C in the test sample are eliminated and, in the second step, the cholesterol remaining in the test sample (viz., LDL) is quantified. In the first step, cholesterol esterase and cholesterol oxidase act on the test sample in the presence of a surfactant that acts on lipoproteins other than LDL-C ("non-LDLs"). The hydrogen peroxide thereby generated is decomposed to water and oxygen by catalase. Alternatively, a phenol-based or aniline-based hydrogen donor is reacted with the hydrogen peroxide to convert it to a colorless compound. Preferred surfactants that act on the non-LDLs include polyoxyethylene lauryl ether, polyoxyethylene cetyl ether, polyoxyethylene oleyl ether, polyoxyethylene higher alcohol ether, and the like. In the second reaction disclosed in the '164 patent, cholesterol remaining in the test sample, which should theoretically contain only LDL-C, is quantified. The second step may be carried out by adding a surfactant that acts on at least LDL and quantifying the resulting hydrogen peroxide by the action of the cholesterol esterase and the cholesterol oxidase added in the first step.

As with the method disclosed in the '827 patent, one disadvantage of the method taught by the '164 patent is that it requires heating the reaction mixture to a temperature of 37° C., and experimental data indicates that the test accuracy suffers at lower temperatures. Also as taught in the '827 patent, the method of the '164 patent requires multiple reagents to be added at different times, making it equally incompatible with POC testing or use in over-the-counter ("OTC") applications.

A homogeneous assay for measuring LDL-C in serum was disclosed by H. Sugiuchi et al., Clinical Chemistry 44:3 522-531 (1998. This disclosure shows a correlation between the use of a combination of triblock copolymer and alpha-cyclodextrin sulfate and the selective enzymatic reaction of LDL-C when both LDLs and non-LDLs are contacted with the combination in a liquid assay system. The preferred polyoxyethylene-polyoxypropylene block copolymer of the Sugiuchi et al. disclosure exhibited limited solubility under liquid assay reaction conditions, rendering the adaptation to a dry strip unworkable.

Co-pending and commonly assigned U.S. patent application Ser. No. 10/663,555, filed Sep. 16, 2003, discloses a one-step, room-temperature whole blood, dry chemistry assay for LDL-C in which the amount of LDL-C present in whole blood is calculated from the results of direct measurements of total cholesterol and non-LDL-C. Although the disclosed assay overcomes most of the problems of the multistep, wet chemistry LDL cholesterol assays of the prior art, there remains a preference for direct assays. Thus, there remains a need for a convenient, easy to use, dry, one-step, room-temperature diagnostic test for directly measuring LDL-C.

SUMMARY OF THE INVENTION

These and other problems of prior art assays for LDL-C are overcome by the present invention. The present invetnion, in one aspect is a direct, room-temperature method for the detection and measurement of cholesterol from low-density lipoproteins in a plasma, serum or whole blood sample. The method comprises treating a sample that includes both LDLs and non-LDLs so that enzymatic conversion of LDL-C is encouraged while enzymatic turnover of non-LDL-C is retarded or blocked. The sample is treated by contacting it with a combination of reagents that relate to LDLs and to non-LDLs differently as a function of their differing surface charge density. Any reagents that correspond with the various lipoproteins in a sample as a function of surface charge density carried by the lipoproteins in such a way that selectively encourages enzymatic conversion of cholesterol carried by LDLs while blocking or retarding such conversion in the other types of lipoprotein cholesterol present may be used.

This invention is based in part onthe discovery that the differeing surface charge density of the LDLs and non-LDLs in a sample can be used to advantage. the sparsely negatively charged surface characteristics, measured at or near physiological pH, of chylomicron, VLDLs, and IDLs cause them to bind to certain anionic polymers and, in particular sulfates. Although good results have been observed in connection with a range of dextran sulfates, a polyanion, having molecular weights from about 5,000 to about 50,000, the best results to date have been obtained when these polyanions are used in conjunction with alpha cyclodextrin sulfate or other cyclodextrin derivatives.

HDL's are found to be generally strongly negatively charged and have been found to be blocked from producing cholesterol, or temporarily protected from the activity of cholesterol-producing enzymes, when bound with specific combinations of such sulfates and with a copolymeric surfactant. Although simple polypropylene glycol and polyethylene glycol molecules are found to also inhibit the enzymatic conversion of HDL-C, the preferred copolymeric surfactant is a polyoxyethylene-polyoxypropylene-polyoxyethylene hybrid, having a molecular weight range from about 2,100 to about 6,000 with a predonderance of polyoxypropylene. Preferably the polyoxypropylene comprises 80-95% of the copolymer surfactant.

Another aspect of the invention is based in part on the discovery that certain lower molecular weight surfactants can be used to increase the solubility of high molecular weight block copolymer surfactants, making them useful in test strip assays for direct measurement of LDL-C. In the present invention, the limited solubility of these preferred compounds has been addressed by the use of a surfactant systerm that in part functions onthree different levels. In the first level, the surfactants of the present invention will aid to solubilize the polyoxyethylene-polyoxypropylene-polyoxyethylene hybrid without diminished selectivity in enzymatic conversion of the LDL-C relative to the non-LDL-C analytes in a sample. The second level of surfactants in part produce mixed micelles that, in a multi-membrane or multi-layer test strip, transport the triblock copolymer and released LDL-C from a reagent-containing membrane to a cholesterol-reaction membrane. The third level of surfactants, which in practice are normally directly adjacent or impregnated on a cholesterol reaction membrane in a test strip, function in part to solubilize or emulsify released cholesterol from the mixed micelles, containing the triblock copolymer and other surfactants, so that the cholesterol can react with the enzyme system of the cholesterol reaction membrane.

Selective treatment of non-LDLs in a sample by such reagents is enabled by the use of a cationic species connecting them selectively to non-LDLs. In one aspect of the invention, the cationic species is a divalent metal bridge. The divalent metal bridge has been observed to link the reagents to the surfaces of non-LDLs, which have a sufficiently dense negative surface charge that the surface charge of the LDLs in the same sample is relatively slightly positive. Although good results have been achieved with magnesium, other divalent metals such as calcium, manganese and others could be used. In addition, any materials that can electrostatically bond to the negatively charged surface of the lipoprotien structures and/or the polyanion can exhibit similar enzymatic selectivity. As an example, good results have been achieved using triethanolamine hydrochloride as the cationic species for the bridging component.

The copolymeric surfactant and other polymeric anions that aid in blocking the production of cholesterol from HDL's are carefully chosen to also initiate the production of cholesterol from the unblocked LDLs.

Measuring the concentrations of the produced cholesterol from LDLs in the blood sample can be done by using already well-known methods and materials. Typical of such methods and materials is the use of Trinder reagents in an enzymatic reaction resulting in a color change described in the co-pending and commonly assigned U.S. patent application Ser. No. 10/663,555, mentioned above, which is based on provisional application No. 60/411,209, filed Sep. 16, 2002.

In another aspect, the present invention comprises a vertical flow test strip for use in the direct detection of cholesterol produced from low density lipoproteins in a serum, plasma or whole blood sample. The test strip includes a mechanism for stopping or retarding the vertical flow of red blood cells contained in the sample. Although any useful mechanism can be used, the best results to date have been achieved using a layer of material that includes non-woven glass fibers. The glass-fiber-containing layer may optionally be covered with a spreading layer that facilitates the spread of blood over an area surrounding the point of application. The purpose of blocking or at least retarding the flow of red blood cells to the reaction membrane surface is to prevent interference with detection of the color change in the detection chemistry at the end of the test.

The test strip also includes a supply of materials that is situated in the vertical flow path of the blood sample and that includes materials that are soluble in the sample and that work together to block or retard the production of cholesterol from non-LDLs while facilitating the production of cholesterol from LDLs. The supply of such materials is normally deposited on one or more layers in the vertical flow path of the blood sample so that the materials are brought into solution following separation of red blood cells from the sample. However, the supply of materials could also be located prior to the red blood cell separation mechanism.

Thematerials are selected to work with the electrical characteristics of the non-LDL components sought to be blocked from the production of cholesterol. Typically, the materials include a divalent metal ion source capable of forming a bridge between the electrically negative components, listed above, while avoiding the formation of such a bridge between LDL in the sample and the protective components due to the diminished anionic electrical surface characteristics normally found in the LDLs.

The test strip also includes, in the flow path of the blood sample and furthest away from the application point, a supply of materials selected to result in a detectible color change following enzymatic conversion of the produced cholesterol.

It is one general object of the invention to provide a dry phase test strip chemistry for testing the concentration of analytes in a body fluid. A more specific object is to provide a dry test strip capable of directly determining the concentration of LDL-C in whole blood or plasma.

One significant benefit of the present invention is that the LDL-C concentration can be directly determined in a single stage assay. Another benefit is that the diagnostic test can be performed at room-temperature. Other benefits and objects of the invention will be discerned upon consideration of the following description of the invention.

DESCRIPTION OF THE PREFERRED EMBODIMENTS

Figure 1:
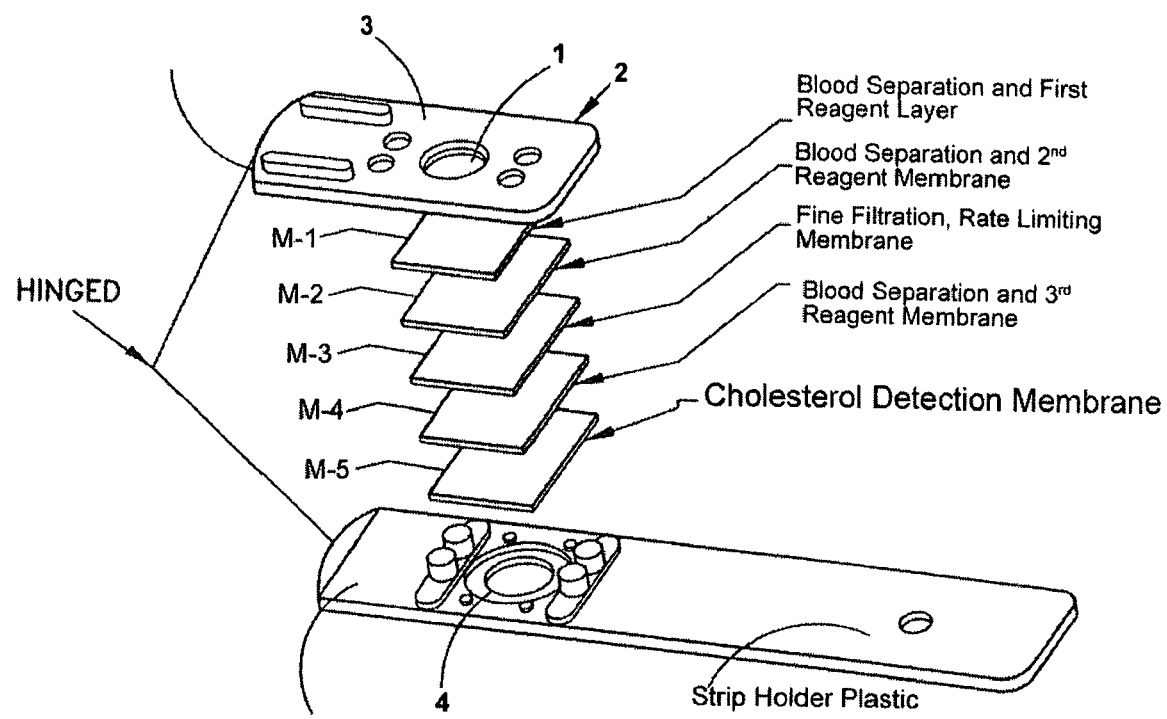
FIG. 1 shows a test strip according to the present invention.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations andmodifications to the illustrated embodiments and includes further applications of the principles of the invention as would normally occur to one skilled in the art to which this invention pertains.

One useful embodiment of the present invention is shown in FIG. 1. Elements or layers M-1, M-2, M-3, M-4 and M-5 are held between sample application port 1 and read port 4 and define the vertical pathway traversed by the sample following the application of serum, plasma or whole blood to at sample application port 1.

In this embodiment, the sample first may encounter an optional spreading layer that is not shown in FIG. 1 but would be directly above Layer M-1. The purpose of spreading layer, if present, is to spread the sample relatively evenly over an area of port 1 that is larger than the application point. In addition, the spreading layer may be impregnated with the above-described reagents. One purpose of impregnation of the spreading layer, if it is present, is to provide alonger contact time between the applied sample and the reagents.

Blood separation layer M-1 is, inthis embodiment, at least a part of the mechanism for blocking or retarding the flow of red blood cells. In a specific example, layer M-1 is a nonwoven glass fiber layer available from Ahlström Corporation, under the trade name "TuffGlass 144". Layer M-1 may contain dextran sulfate, a divalent metal or equivalent, cyclodextrin molecules, buffers, solubilizers such as sorbitol or sucrose and surfactants, including but not limited to the copolymer or triblock polymer surfactants that exhibit LDL or non-LDL selectivity.

Like layer M-1, Layer M-2 can also function to limit or retard the movement of red blood cells through the test strip and corresponding membranes. M-2 is typically an asymmetric polysulfone membrane with a high degree of asymmetry. In the preferred embodiment of this invention, the membrane is BTS SP-300 available from Pall Life Sciences. This layer may also contain each of the elements described in M-1 with the addition of reagents in concentrations that are markedly different than M-1. In addition, surfactants may be present to increase the mobility of cholesterol released from the lipoprotein structures. Specifically, M-2 may contain all or part of the polyanion such as the dextran sulfate, a divalent or other cationic species required for proper blocking of non-LDLs, all or part of the cyclodextrin molecules, surfactants, and in particular all or part of the copolymer or triblock polymer utilized to block HDL-C and/or make LDL-C available. As with the layer M-1, layer M-2 may also include solubilizers, such as Sorbitol and sucrose.

The supply of divalent metal or other cationic species can originate from either M-1, M-2 or the spreading mesh, although the preferred location is M-2 or additionally M-4. The divalent metal may be, for example, calcium, magnesium or manganese. The most preferred cation is magnesium, which was chosen for its low cost, availability and ease of handling. The cationmay also be a positively charged amine capable of binding lipoproteins. One preferred amin is a tertiary amine such as triethanoiamine.

In the embodiment shown in FIG. 1, layer M-2 is also a blood separation layer. It is an asymmetric material with a pore size of 300 microns on the sample-receiving side and about three (3) microns on the detection side. In addition to helping block or retard the flow of red blood cells, it also slows the flow of the entire blood sample along the vertical path to increase the contact time of the sample with the reagents.

Like M-2, the element identified in FIG. 1 as M-3 is a membrane that slows the rate of flow of the applied through the vertical arrangement so as to increase the amount of time the sample is in contact wioth the reagent membranes although this membrane rarely is treated with reagents designed to impart lipoprotein selectivity. The desing objective for M-3 is controlled kydrophilicity and pore size to attenuate flow of the sample material thorugh the test strip. A number of different membranes have been effective to this end although the membrane of choice is hydrophilic polyether sulfone with a trade name of Supor 1200 available from Pall Life Sciences. Also especially effective membranes of element M-3 are track-etched polycarbonate membranes such Poretics 0.4 Micron from Osmonics Inc. In most cases, this membrane is untreated except for surfactants or other wetting agents that may facilitate the spreading of the sample across the membrane surface.

The element designated in FIG. 1 as M-4 is also a reagent membrane layer and can optionally contain the same reagents as M-2 although in different proportions. Like M-2 the preferred membrane is an asymmetric polysulfone like BTS SP-300 available from Pall Life Sciences. In some examples of the present invention, M-4 can be optional depending at least in part on the composition, reagents and arrangements of the elements M-1, M-2, M-3 and the optional spreading mesh not illustrated in FIG. 1.

The layer illustrated as M-5 in FIG. 1 is the cholesterol detection membrane, which may be the membrane described in the co-pending and commonly assigned U.S. patent application No. 10/663,555, filed Sep. 16, 2003.

EXAMPLE 1

A dry strip was constructed based on the following membranes and arrangement relative to FIG. 1:

Layer M-1; Tuffglass impregnated as described in "Part A".

Layer M-2; BTS-300 impregnated as described in "Part B".

Layer M-3 ; Supor 1200, untreated

Layer M-4; BTS-300 impregnated as described in "Part B".

Layer M-5; Biodyne A, as described in the co-pending and commonly assigned U.S. patent application No. 10/663,555, filed Sep. 16, 2003.

M-1, Tuffglass was dipped in solution "Part A" and was dried with moving air at 38° F. ±2.5° C.

Part A

To 300 mL of laboratory D.I. water the following was added: MES buffer 3.50 g, Sorbitol 9.0 g, sucrose, 9.0 g, polyethylene glycol 200 mwt 7.0 g. dextran sulfate 10K mwt. 10.03 g, NaCl 2.01 g. The pH of the solution was adjusted to a pH of 5.90 +/−0.1 with 5 N NaOH. A total of 2.80 m of 5 N NaOH was added to give a final pH was 5.85.

From this stock solution, 169.89 grams were removed and placed in a 250 mL beaker. To this beaker, 2.0 g of dextran sulfate 10K mwt were dissolved. The pH was adjusted with 760 µL 5 N NaOH to give a final pH of 5.95. The Tuffglass was dipped into this solution and was hung vertically to allow the excess solution to drip off the membrane. The membrane was then placed in the clipboard and dried horizontally in the dyring tunnel using standard heated conditions.

Part B

To 200.15 g laboratory D.I. water the following wad added in order: MES buffer 2.0 g, Sorbitol 9.06 g MgCl$_2$-6H$_2$0 7.04 g. The pH was adjusted to 6.03 with 1.025 mL of 5 N NaOH. The solution was then chilled to 5° C. followed by the addition of the following: α-cyclodextrin sulfate 1.38 g, Silwet L-77 0.73 g, Pluronic L121 1.66 g, Pluronic L43 0.45 g. The solution was kept chilled during all additions. The Pyrex glass dish used to dip the membrane was chilled in the freezer before the addition of the impregnation reagent mixture. Approximately 70 mL of the "Part B" solution was added to the chilled glass vessel. Themembranes were dipped and hung vertically for drying. Excess reagent was allowed to drip from the membrane that was drived without heat or application of moving air.

Figure 2:
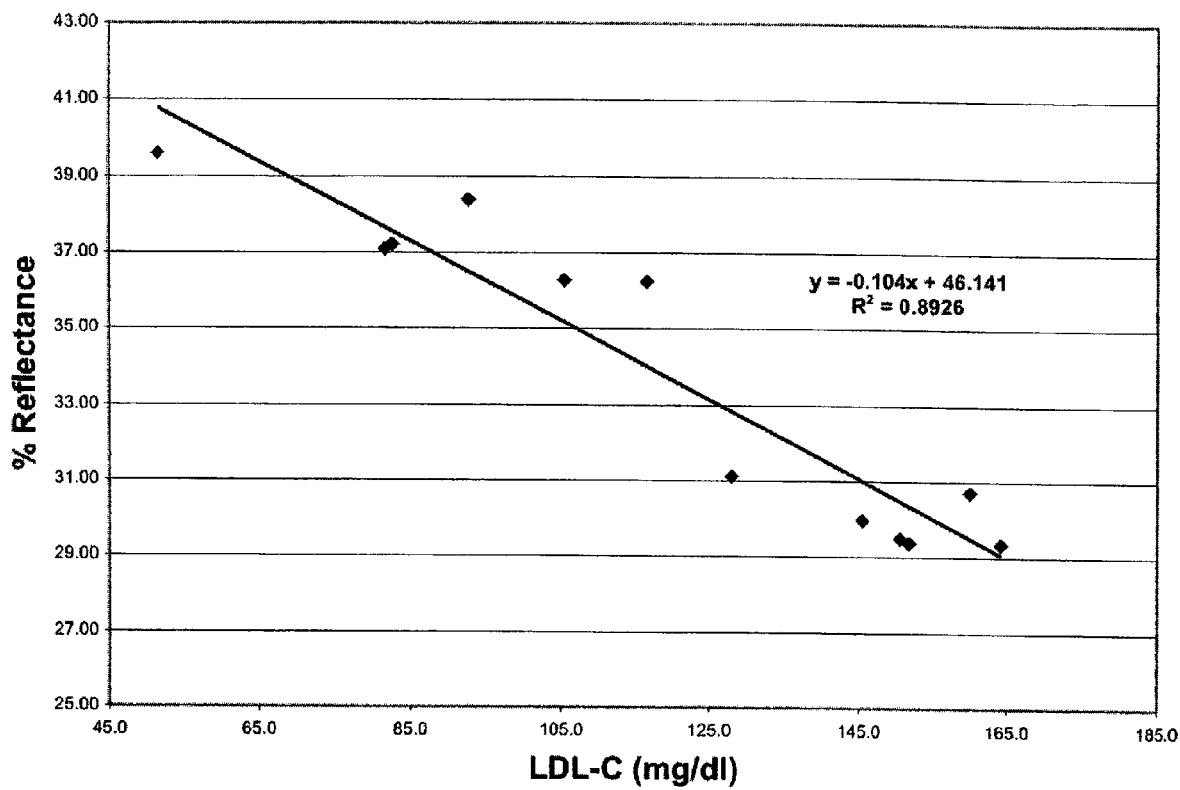
FIG. 2 shows the correlation between LDL-C as determined by gel electrophoresis and a measured %R obtained by dry test strips prepared according to one embodiment of the present invention identified as Example 1.

FIG. 2 illustrates the data generated from the construction of the strip of Example 1 using twelve different blood samples with the results of each sample being an average of six strip results. Control aliquots of the same sample were tested for LDL-C by gel electrophoresis. The correlation between these control aliquots and the assays performed according to the method and device of the present invention was found to be good, as shown in FIG. 2.

EXAMPLE 2

A dry strip was constructed based on the following membranes and arrangement relative to FIG. 1:

Layer M-1; Tuff Glass Impregnated as described in "Part C".

Layer M-2; Not present.

Layer M-3; Supor 1200, untreated.

Layer M-4; BTS SP300 impregnated as described in "Part D".

Layer M-5; Biodyne A.

Part A

The following solution was impregnated onto a depth filter, which can encompass an amorphous fiber or a composite material of either glass, polymer or a random composite matrix. The impregnation can be by any known methods, such as dipping, spraying or freeze drying to produce the top reagent layer of the dry strip.

To 50 mL of D.I. water the following were added: 1.23 g of MOPS buffer, 1.5 g dextran sulfate with an average molecular weight of 10,000, 0.5 g α-cyclodextrin sulfate, 2.99 g Sorbitol 3.0 g sucrose, and 0.6 g magnesium chloride, all in 50 ml of D.I. water. The pH was adjusted to 7.17 using 1 ml of 5N NaOH.

Part D

The following solution was impregnated onto a membrane that can be in part also utilized to separate red blood cells from a whole blood sample to yield either plasma or serum to the detection layer M-5 as well as to control reagent reconstitution either in the presently treated membrane or a subsequent reagent treated membrane or other substrate.

To 300 mL of D.I. water, the following reagents were added: 6.01 g Pluronic L121, 4.32 g magnesium chloride, 3.0 g MPOS buffer, 4.13 g alpha-cyclodextrin sulfate, 0.63 g MOPS buffer, 1.08 g Sorbitol, 1.11 g sucrose, 0.47 mg Silwet L-77. The pH of the solution was 6.95 unaltered. The cloud point of the solution was 20° C. The layer was treated with 60.09 g of this solution.

EXAMPLE 3

A dry strip was constructed based on the following membranes and arrangement relative to FIG. 1:

Layer M-1; Tuff Glass impregnated as described in "Part E".

Layer M-2; BTS SP300 impregnated as described in "Part F"

Layer M-3; Supor 1200, untreated.

Layer M-4; Not present.

Layer M-5; Biodyne A.

Part E

To 50 mL of D.I. water the following were added: 1.2 g of MOPS buffer, 2.5 g dextran sulfate 10K, 0.5 g alpha-cyclodextrin sulfate, 2.01 g Sorbitol, 2.0 g sucrose, and 0.6 g magnesium chloride. The pH was adjusted to 7.16 using 1 ml of 5 N NaOH.

Part F

To 300 mL of D.I. water, the following reagents were added: 6.19 g Pluronic L121, 3.22 g magnesium chloride, 3.0 g MOPS buffer, 4.0 g alpha-cyclodextrin sulfate, 0.55 g MOPS buffer, 1.1 g Sorbitol, 1.12 g sucrose, 1.88 g Silwet L-77, 1.05 g Pluronic L121. The final pH of the unaltered solution was 7.0. The layer was treated with 60.09 of this solution.

EXAMPLE 4

A dry strip for this example was constructed with the same membranes as in Example 3, namely Tuff Glass (M-1), BTS SP300 (M-2), Supor 1200 (M-3), and Cholesterol reaction membrane (M-5).

The Tuff Glass layer (M-1) was treated with 4.32 g of MOPS buffer, 8.87 g dextran sulfate 10K, 0.5 g alpha-cyclodextrin suflate, 9.9 g Sorbitol, 11.25 g sucrose, and 2.28 g magnesium chloride, 7.4 g Polyethylene Glycol, in 168.33 g of deionized water. The pH was adjusted to 7.11 using 0.4 ml of 5N NaOH.

The BTS SP300 layer (M-2) was treated with 30.02 g of the following solution: 5.42 g Pluronic-L121, 7.05 g magnesium chloride, 2.0 g MOPS buffer, 4.592 g α-cyclodextrin sulfate, 0.91 g Sorbitol, 0.75 g hydroxypropyl cellulose, 1.38 g dextran sulfate 10K, 2.47 g Silwet L-77 in 100 ml of deionized water, to which was added 0.33 g MOPS buffer, 0.65 g Sorbitol, 0.67 g sucrose, ~29 mg Silwet L-77, 0.09 g Tetronic 1107. The final pH of the solution was 7.27 with 0.1 ml of 5N NaOH. There was no treatment to the Supor 1200.

EXAMPLE 5

A dry strip for this example was constructed with the same membranes as in Example 3, namely Tuff Glass (M-1), BTS SP300 (M-2), Supor 1200 (M-3), and Cholesterol reacation membrane (M-5).

The Tuff Glass layer (M-1), was treated with 0.35 g Pluronic L121, 0.06 g Tetronic 304, 1.56 g of MES buffer, 3.11 g dextran sulfate 10K, 0.7687 g alpha-cyclodextrin sulfate,. 2.51 g Sorbitol, 1.17 g sucrose, and 1.1 g magnesium chloride, 0.1 ml Silwet L-77, in 75.0 g of deionized water. The pH was adjusted to 6.14 using 0.4 ml of 5N NaOH.

The BTS SP300 (M-2), was treated with 1.80 g Pluronic L121, 0.91 g dextran sulfate 10K, 0.7477 g alpha-cyclodextrin sulfate, 0.8 g MOPS buffer, 2.0 g Sorbitol, 0.61 g sucrose, 0.9 g magnesium chloride, 0.29 g Tetronic 1107 all in 75 g of deionized water. The final pH of the solution was 7.17 with 0.15 ml of 5N NaOH. There was not treatment to the Supor 1200.

EXAMPLE 6

A dry strip was constructed based on the following membranes and arrangement relative to FIG. 1:

Layer M-1; Tuff Glass impregnated as described in "Part G", subsequently impregnated as described in "Part H", and subsequently treated as described in "Part I".

Layer M-2, BTS SP300 impregnated as described in "Part J subsequently impregnated as described in "Part K", and subsequently treated as described in "Part I".

Layer M-3; Supor 1200, untreated.
Layer M-4; Not present.
Layer M-5; Biodyne A.

Part G

To 1875.0 g of D.I. water the following were added: 8.95 g Pluronic L121, 17.85 g Tetronic 304, 39.1 g of MES buffer, 77.64 g dextran sulfate 10K, 19.2 g alpha-cyclodextrin sulfate, 62.5 g Sorbitol, 29.11 g sucrose, and 27.35 g magnesium chloride, 2.5 g Silwet L-77. The pH was adjusted to 6.14 using 0.4 ml of 5N NaOH.

Part H

The following solution was used to treat the membrane impregnated with Part G, To 199.6 g of D.I. water the following were added: 8.16 g dextran sulfate 10K, 1.41 g alpha-cyclodextrin sulfate, 1.85 g magnesium chloride, 3.45 g MES buffer, 3.14 g Sorbitol. The pH was adjusted to 6.24 using 1.4 ml 5N NaOH.

Part I

A 2.0% polyvinyl alcohol solution was prepared to subsequently treat both Layer M-1 and Layer M-2.

Part J

To 749.8 g of D.I. water, the following chemicals were added: 16.1 g Pluronic L121, 9.0 g dextran sulfate 10K, 5.0 g alpha-cyclodextrin sulfate, 7.9 g MOPS buffer, 12.8 g Sorbitol, 4.7 g sucrose, 7.0 g magnesium chloride, 3.42 g Tetronic 1107, 2.2 g Silwet L-77. The final pH of the solution was 7.22 with 3.0 ml of 5N NaOH.

Part K

To 100 g of D.I. water the following chemicals were added. 1.5 Silwet L-77 g, 1.05 Pluronic L121.

EXAMPLE 7

Dry test strips were composed of the same membranes as in Example 3, namely: Tuff Glass (M-1), BTS SP300 (M-2), Supor 1200 (M-3), and Cholesterol reaction membrane (M-5). The Tuff Glass layer (M-1) was treated with 64.6 g Pluronic L121, 5.79 g Tetronic 304, 12.58 g of MES buffer, 24.97 g dextran sulfate 10K, 6.16 g alpha-cyclodextrin sulfate, 20.0 g Sorbitol, 9.3 g sucrose, and 8.77 g magnesium chloride, 0.79 g Silwet L-77, in 599.63 g of deionized water. The pH was adjusted to 6.21 using 5.5 ml 5N NaOH.

The BTS SP300 (M-2) in this example was treated with 3.6 g Pluronic L121, 2.02 g dextran sulfate 10K, 1.53 g alpha-cyclodextrin sulfate, 1.78 g MOPS buffer, 1.21 g Sorbitol, 1.29 g sucrose, 1.81 g magnesium chloride, 0.62 g Tetronic 1107, 1.03 g Emulgen 210P, 1.51 g hydroxypropyl (β-cyclodextrtin all in 201.5 g deionized water. Both of these membranes (M-1 and M-2) were run through a drying tunnel. There was no treatment to the Supor 1200.

EXAMPLE 8

Dry test strips were composed of the same membranes as in Example 3, namely: Tuff Glass (M-1) BTS SP300 (M-2), Supor 1200 M-3), and Cholesterol reaction membrane (M-5). The Tuff Glass layer (M-1) was treated with 0.35 g Pluronic L121, 0.06 g Tetronic 304, 1.56 g of MES buffer, 3.11 g dextran sulfate 10K, 0.7687 g alpha-cyclodextrin sulfate, 2.51 g Sorbitol, 1.17 sucrose, and 1.1 g magnesium chloride, 0.1 ml Silwet L-77, in 75.0 g of deionized water. The pH was ajusted to 6.14 using 0.4 ml of 5N NaOH.

The BTS SP300 (M-2) was treated with 1.80 Pluronic L121, 0.91 g dextran sulfate 10K, 0.7477 g alpha-cyclodextrin sulfate, 0,8 g MOPS buffer, 2.0 g Sorbitol, 0.61 g sucrose, 0.9 g magnesium chloride, 0.29 g Tetronic 1107 all in 75 g of deionized water. the final pH of the solution was 7.17 with 0.15 ml of 5N NaOH. There was no treatment to the Supor 1200.

EXAMPLE 9

The dry strips of this example were composed of a non-glass fiber top layer (M-1), namely Accuwick Ultra, followed by a BTS SP300 layer (M-2), a BTS SP300 layer (M-4), and Cholesterol Detection Membrane (M-5). The Accuwick Ultra layer was treated with a solution of the following chemicals dissolved into 375 g of deionized water: 7.80 g of MES buffer, 15.57 g dextran sulfate 10,000 mwt, 3.85 g α-cyclodextrin sulfate, 12.5 g D-Sorbitol, 5.82 g sucrose, 5.47 g magnesium chloride, 1.79 g of Pluronic L121, 3.59 g Tetronic 304, and 0.5 g of Silwet L-77. The pH was adjusted to 6.16 using 2 ml of 5N NaOH.

The first BTS SP300 layer (M-2) was impregnated by dipping and rolling away the excess the following solution: into 187.5 g of deionized water the following chemicals were dissolved; 2.18 g PVA 30-70K mwt, 1.75 g Tetronic 304, 402 g MES buffer, 7.77 b Dextralip 15, 1.96 g α-cyclodextrin sulfate, 7.31 g D-Sorbitol, 1.40 g sucrose, 3.52 g $MgSO_4$, 2.5 g polyethylene glycol 6,000 mwt, 57 mg Antifoam C. The pH of the above solution was adjusted to 6.27 with 1.5 ml of 5 N NaOH.

The second BTS SP300 layer (M-4) was treated with a solution consisting of the following chemicals dissolved in two solutions. The first solution consisted of 20.35 g of a 4% PVA 3D-70K mwt solution and 30.55 g of a solution containing the following chemicals dissolved into 50.01 g of deionized water: 2.048 g PVA 30-70K mwt, 2.31 g Pluronic L121, 1.20 g dextran sulfate 10,000 mwt, 1.25 g magnesium sulfate, 1.31 g Bis Tris buffer, 1.04 g g α-cyclodextrin sulfate, 3.75 g of D-Sorbitol, 0.0256 g Silwet L-77, and 0.03 g of Tetronic 30, 0.47 g of CHAPS. The pH of the solution was 6.48 after adding ~2.5 ml of 3.25 N HCL.

Figure 3:
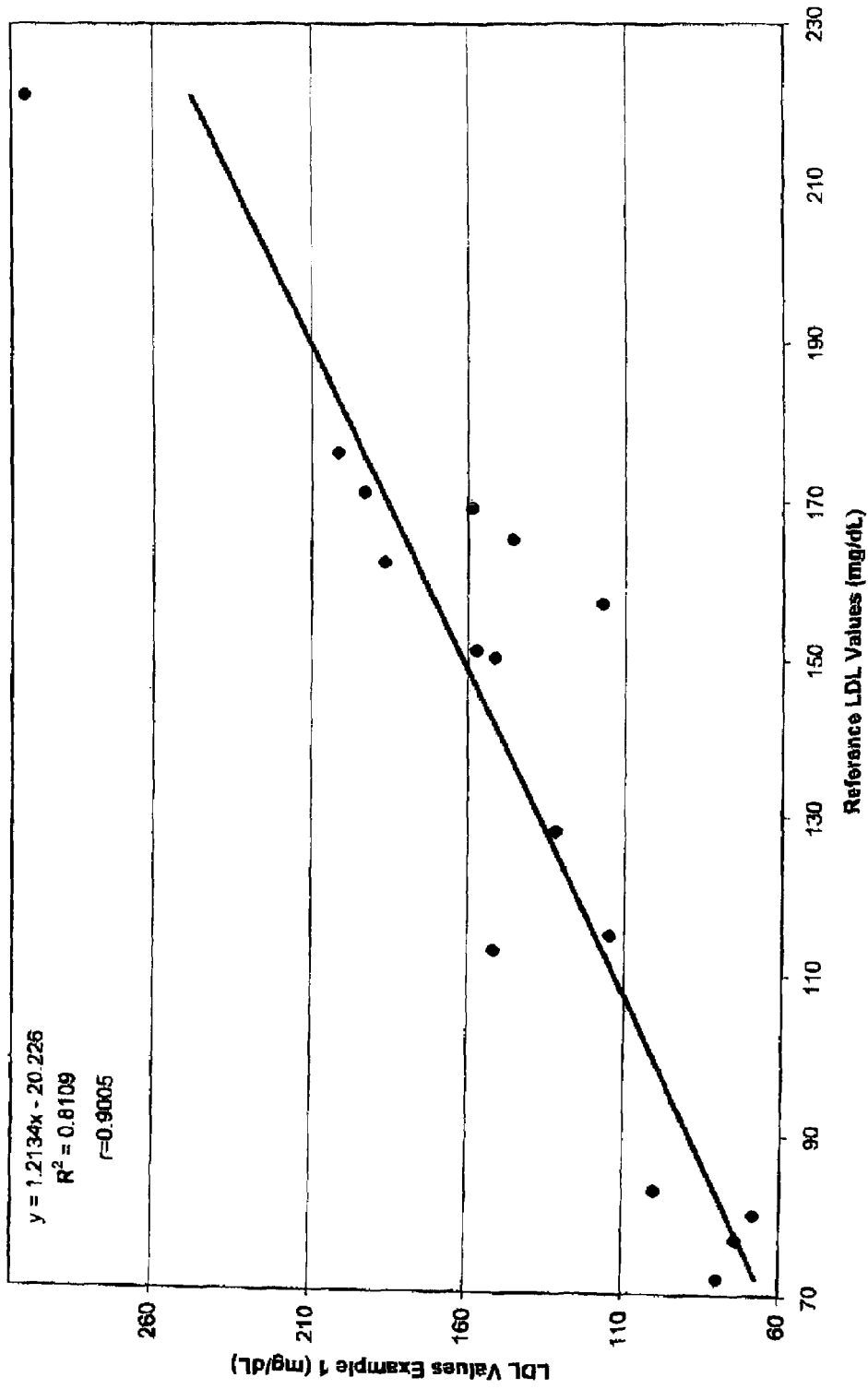
FIGS. 3-9 show the correlation between LDL-C as determined by gel electrophoresis and a measured %R obtained by dry test strips prepared according other embodiments of the present invention identified as Examples 9-15.

The correlation between control aliquots and sixteen assays using the test strips of Example 9 was found to be good, as shown in FIG. 3.

EXAMPLE 10

The dry strips of this example were composed of Tuff Glass (M-1), BTS SP300 (M-2), Supor 1200 (M-3), and Cholesterol Detection Membrane (M-5). the Tuff Glass layer (M-1) was treated with a solution of the following chemicals dissolved into 300 g deionized water: 6.27 g of MES buffer, 12.41 g dextran sulfate 10K, 3.06 g α-cyclodextrin sulfate, 10.01 g D-Sorbitol, 4.65 g sucrose, 4.37 g magnesium sulfate, 1.43 g of Pluronic L121, 2.90 g Tetronic 304, and 0.4 g of Silwet L-77. The pH was adjusted to 6.15 using 1.8 ml of 5N NaOH.The BTS SP300 was treated with a solution of the following chemicals dissolved into 296.5 g of deionized water: 7.20 g Pluronic L121, 3.6 g dextran sulfate 10K, 3.58 g magnesium sulfate, 3.15 g MOPS buffer, 3.20 g α-cyclodextrin sulfate, 8.13 g of D-Sorbitol, 2.38 g sucrose, and 1.2 g Tetronic 304. The pH of the solution was 7.12 after adding 1 ml of 5N NaOH. There was no treatment to the Supor 1200.

Figure 4:
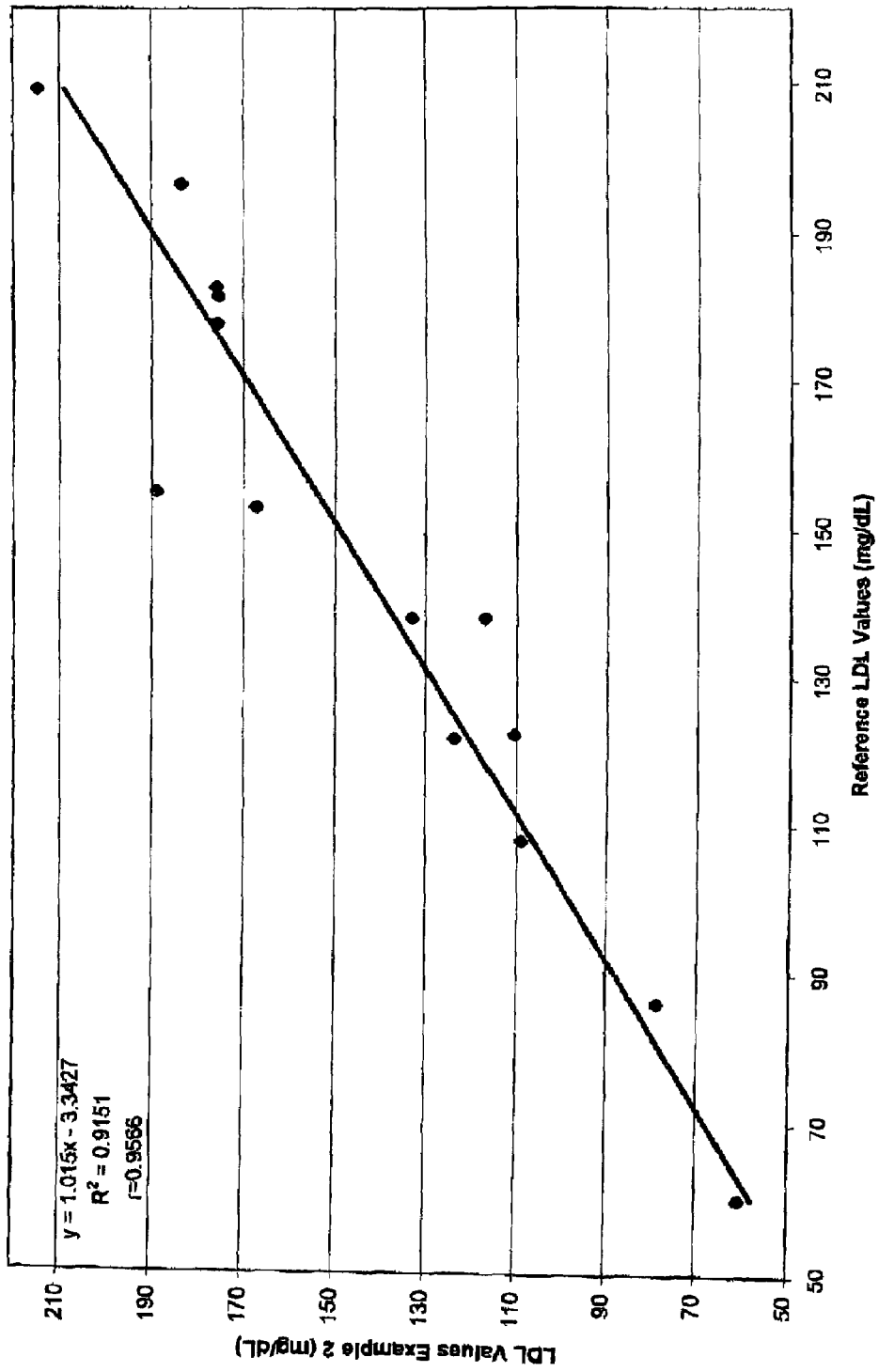

The correlation between control aliquots and fourteen assays using the test strips of Example 10 was found to be good, as shown in FIG. 4.

EXAMPLE 11

The dry strips of this example were composed of Tuff Glass (M-1), BTS SP300 (M-2), Supor 1200 (M-3), and Cholesterol Detection Membrane (M-5). The Tuff Glass layer (M1) was treated with a solution of the following chemicals dissolved into 300 g of deionized water: 6.67 g of MES buffer, 12.57 g dextran sulfate 10K, 3.07 g α-cyclodextrin sulfate, 10.08 g D-Sorbitol, 5.33 g sucrose, 4.41 g magnesium sulfate, 2.86 g Tetronic 304, and 0.0710 g of sodium azide. the pH was adjusted to 6.22 using 2.25 ml of 5N NaOH. This solution was applied to the membrane by dipping into the solution followed by rolling the excess off between two rollers, and allowed to air dry on an open fiber matrix.

The BTS SP300 (M-2) was treated with a solution of the following chemicals dissolved into 500 g of deionized water: 12 g Pluronic L121, 5.99 dextran sulfate 10K, 5.99 g magnesium sulfate, 5.18 g MOPS buffer, 5.19 g α-cyclodextrin sulfate, 4.01 g of D-Sorbitol, 4.01 g sucrose, and 1.9 g Tetronic 304. The pH of the solution was 7.19 after adding 1.5 ml of 5N NaOH. Lastly, the BTS SP300 was then sprayed with a treatment of 4.03 g dextran sulfate 10K, 0.6 g of α-cyclodextrin sulfate, 0.57 g magnesium sulfate, 1.75 g of MES buffer, and 2.0 g D-Sorbitol dissolved into 100.1 g of deionized water. The pH of the solution was 6.31 after adding 1.5 ml of 5N NaOH. There was no treatment of the Supor 1200.

Figure 5:
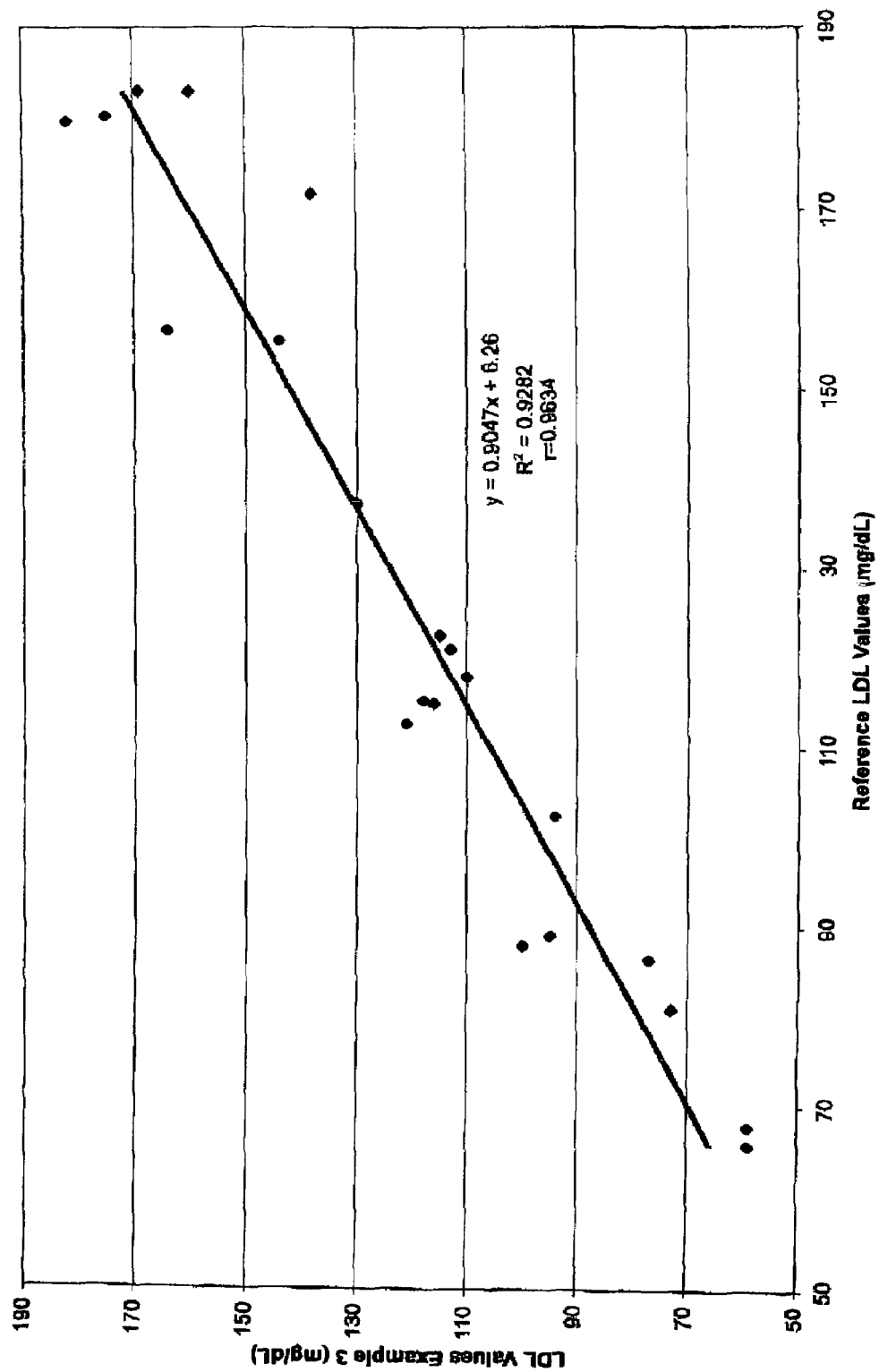

The correlation between control aliquots and twenty-one assays using the test strips of Example 11 was found to be good, as shown in FIG. 5.

EXAMPLE 12

The dry strips of this example were composed of Tuff Glass (M-1), BTS SP300 (M-2), Supor 1200 (M-3), and Chloesterol Detection Membrane (M-5). The Tuff Glass layer (M1) was treated with a solution of chemical reagents dissolved into 300 ml of deionized water: 6.67 g of MES buffer, 12.57 g dextran sulfate 10K, 3.07 g α-cyclodextrin sulfate, 10.08 g Sorbitol, 5.33 g sucrose, 4.41 g magnesium sulfate, 2.86 g Tetronic 304, and 0.0710 g of sodium azide. The pH was adjusted to 6.22 using 2.25 ml of 5NaOH.

The BTS SP300 (M-2) was treated with a solution resulting by dissolving the following chemicals into 500 g of deionized water: 12 g Pluronic L121, 5.99 g magnesium sulfate, 5.18 g MOPS buffer, 5.19 g α-cyclodextrin sulfate, 4.01 g of Sorbitol, 4.01 g sucrose, 5.99 g dextran sulfate 10K and 1.9 g Tetronic 304. The pH of the solution was 7.19 after adding 1.5 ml of 5N NaOH. In additon, 0.50 g of a solution containing the following: 9.99 g Pluronic L123, 10.01 g of Pluronic L101, 5.05 g Pluronic L103, 9.99 g Pluronic L61, 10.02 Pluronic L64, and 2.75 g of Silwet L-77 were added to the BTS SP300 solution before impregnation. After the membrane was dried, it was then sprayed with the following chemicals dissolved into 100 g of D.I. water: 4.03 g of dextran sulfate 10K mwt, 0.6 g α-cyclodextrin sulfate, 0.57 g magnesium sulfate, 1.75 g MES buffer and 2.0 g D-Sorbitol. The pH of the solution was 6.31 after adding 1.5 ml of 5N NaOH. Lastly, the BTS SP300 was then sprayed with a treatment consisting of 4.03 g dextran sulfate 10K, 0.6 g of α-cyclodextrin sulfate, 0.57 g magnesium sulfate, 1.75 g of MES buffer, and 2.0 g Sorbitol. The pH of the solution was 7.19 after adding 1.5 ml of 5N NaOH. There was no treatment to the Supor 1200.

Figure 6:
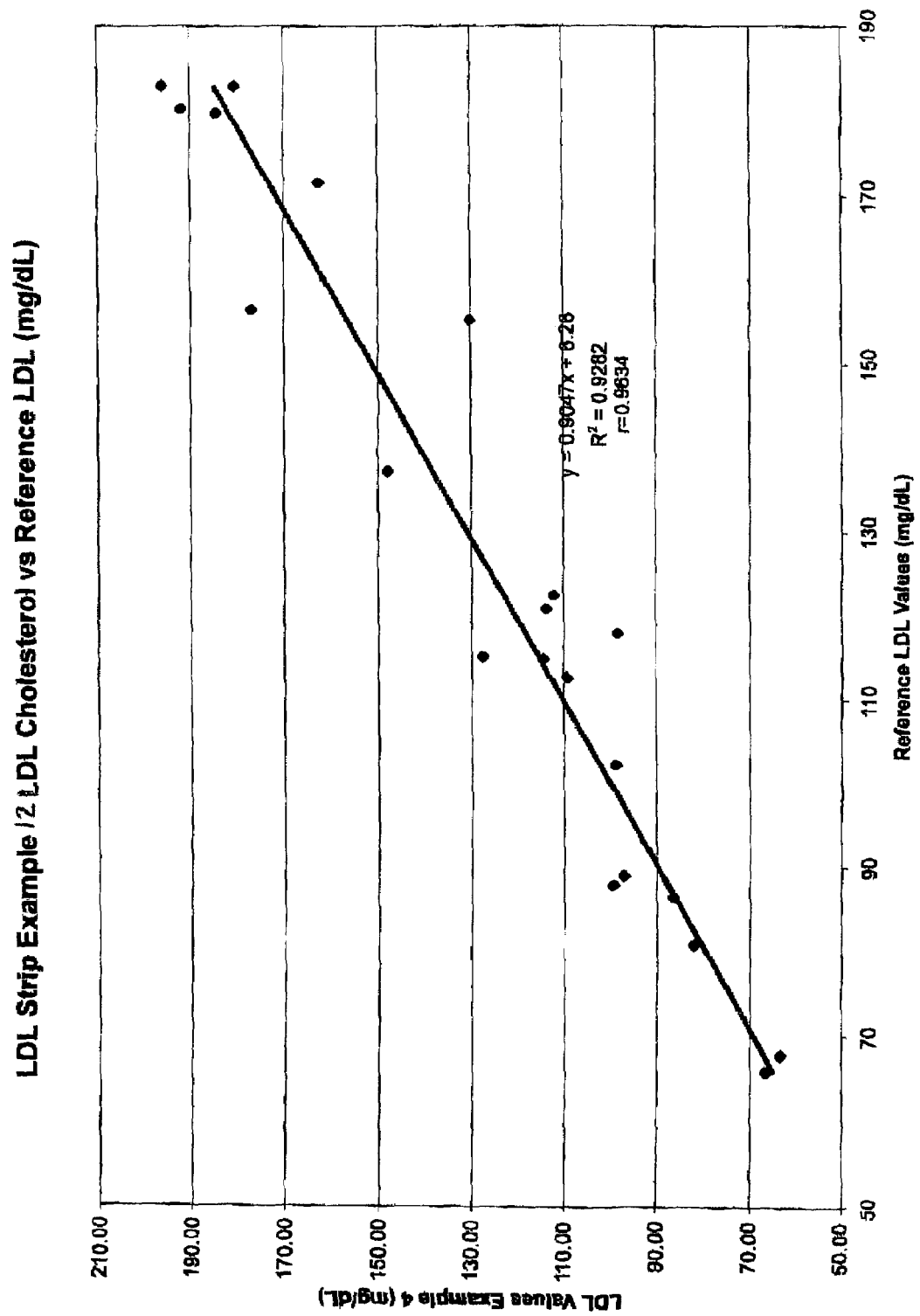

The correlation between control aliquots and twenty-one assays using the test strips of Example 12 was found to be good, as shown in FIG. 6.

EXAMPLE 13

The dry strips of this example were composed of Tuff Glass (M-1), BTS SP300 (M-2), Supor 1200 (M-3), and Cholesterol Membrane (M-5). The Tuff Glass layer (M-1) was treated with 6.67 g of MES buffer, 12.57 g dextran sulfate 10K, 3.07 g α-cyclodextrin sulfate, 10.08 g Sorbitol, 5.33 g sucrose, 4.41 g magnesium sulfate, 2.86 g Tetronic 304, and 0.0710 of sodium azide all in 300 ml of deionized water. the pH was adjusted to 6.22 using 2.25 ml of 5N NaOH. After the membrane had dried, the Tuff Glass was then sprayed with a treatment of 4.03 g dextran sulfate 10K 0.6 g of α-cyclodextrin sulfate, 0.57 g magnesium sulfate, 1.75 g of MES buffer, and 2.0 g D-Sorbitol all in 100 g of deionized water. The pH was adjusted to 6.31 with 1.5 ml of 5N NaOH.

The BTS SP300 (M-2) was treated with 18.8 g Pluronic L121, 2.90 g magnesium sulfate, 7.37 g MOPS buffer, 8.96 g α-cyclodextrin sulfate, 7.38 g of Sorbitol, 6.00 g sucrose, 10.11 dextran sulfate 10K, 7.12 g Tetronic 304, 2.90 g Silwet L-77 and 0.15 g sodium azide, all dissolved in 749.5 g of deionized water. The pH of the solution was 7.15 after adding 2.5 ml of 5N NaOH. In addition, 1.50 g of the following solution was added to the above solution before impregnation: 9.99 g Pluronic L123, 10.01 g Pluronic L101, 5.05 g Pluronic L103, 9.99 g Pluronic L61, 10.02 g Pluronic L64, and 2.75 g Silwet L-77. After the membrane had dried, it was spryaed with the following chemicals dissolved into 100 g of D.I. water: 4.03 g dextran sulfate 10K mwt, 0.06 go of α-cyclodextrin sulfate, 0.57 g magnesium sulfate, 1.75 g of MES buffer, and 2.0 g Sorbitol. There was no treatment to the Supor 1200.

Figure 7:
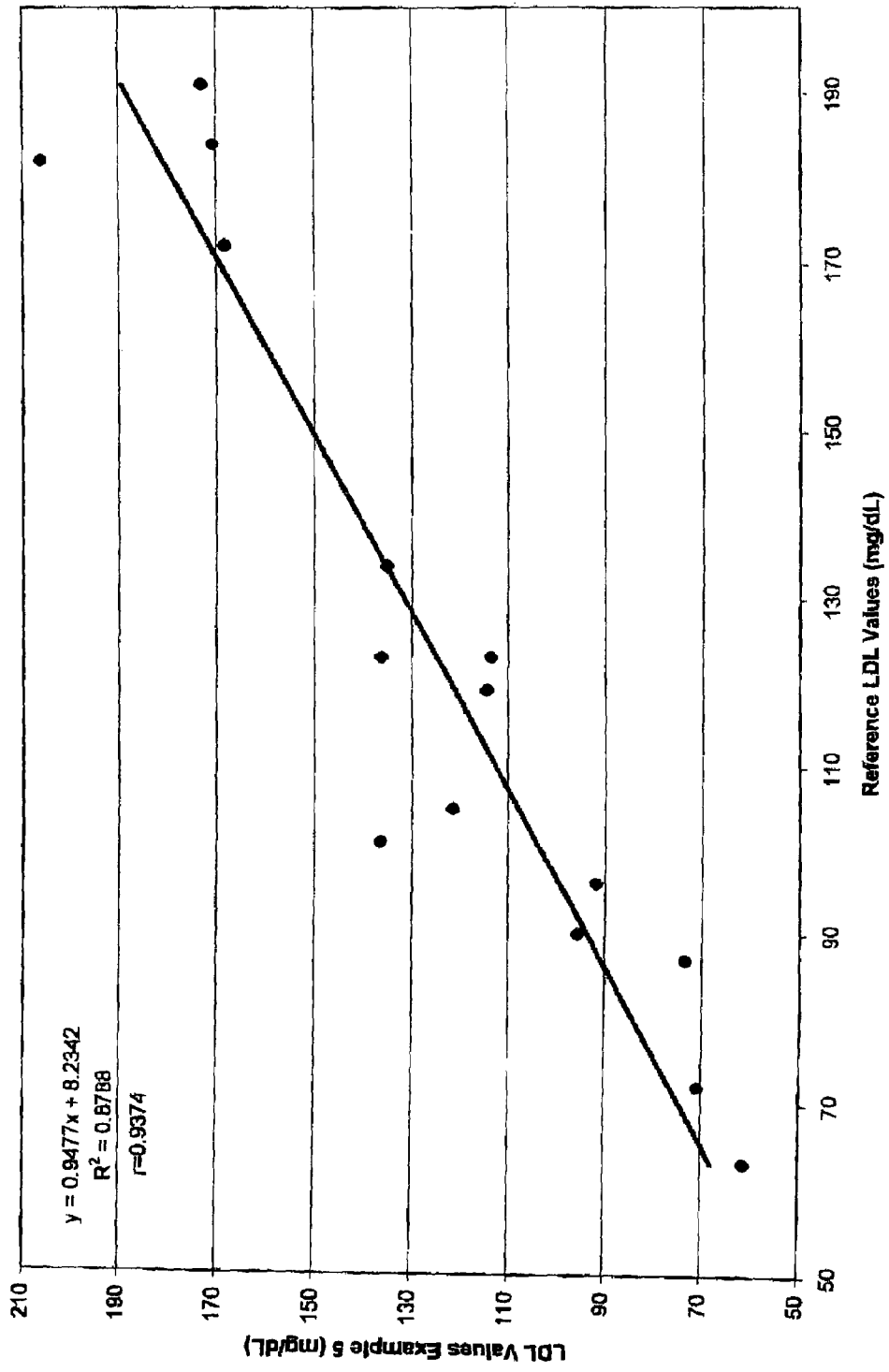

The correlation between control aliquots and fifteen assays using the test strips of Example 13 was found to be good, as shown in FIG. 7.

EXAMPLE 14

The dry strips of this example were composed of Tuff Glass (M-1), BTS SP300 (M-2), Supor 1200 (M-3), and Chloesterol Membrane (M-5). The Tuff Glass layer (M-1) was treated with 6.6 g of MES buffer, 12.57 g dextran sulfate 10K, 3.07 g α-cyclodextrin sulfate, 10.08 g Sorbitol, 5.33 g sucrose, 4.41 g magnesium sulfate, 2.86 g Tetronic 304, and 0.0710 of sodium azide all in 300 ml of deionized water. The pH was adjusted to 6.22 using 2.25 ml of 5N NaOH. After the membrane had dried, the Tuff Glass was then sprayed with a treatment of 4.03 g dextran sulfate 10K, 0.6 g of α-cyclodextrin sulfate, 0.57 g magnesium sulfate, 1.75 g of MES buffer, and 2.0 g Sorbitol dissolved in 100 g of deionized water. The pH was adjusted to 6.31 with 1.50 ml of 5N NaOH. The Tuff Glass was next sprayed with a 2% solution of PVA.

The BTS SP300 (M-2) was treated with 18.8 g Pluronic L121, 2.90 g magnesium sulfate, 7.37 g MOPS buffer, 8.96 g α-cyclodextrin sulfate, 7.38 g of Sorbitol, 6.00 g sucrose, 10.11 g dextran sulfate 10K, 2.90 g Silwet L-77, 7.12 g Tetronic 304, and 0.15 g of sodium azide, all in 749.5 g of deionized water. The pH of this solution was adjusted to 7.15 by 2.5 ml of 5N NaOH. When dried, the BTS SP300 was then sprayed with a treatment of 24.00 g dextran sulfate 10K, 3.57 g of α-cyclodextrin sulfate, 3.58 g magnesium sulfate, 10.78 g of MES buffer, and 11.82 g D-Sorbitol dissolved in 600 g of deionized water. The pH was adjusted to 6.20 with 2.0 ml of 5N NaOH. Lastly, the BTS SP300 (M-2) was then sprayed with a treatment of 0.15% Silwet L-77 and 1.0% Pluronic L121. There was no treatment to the Supor 1200.

Figure 8:
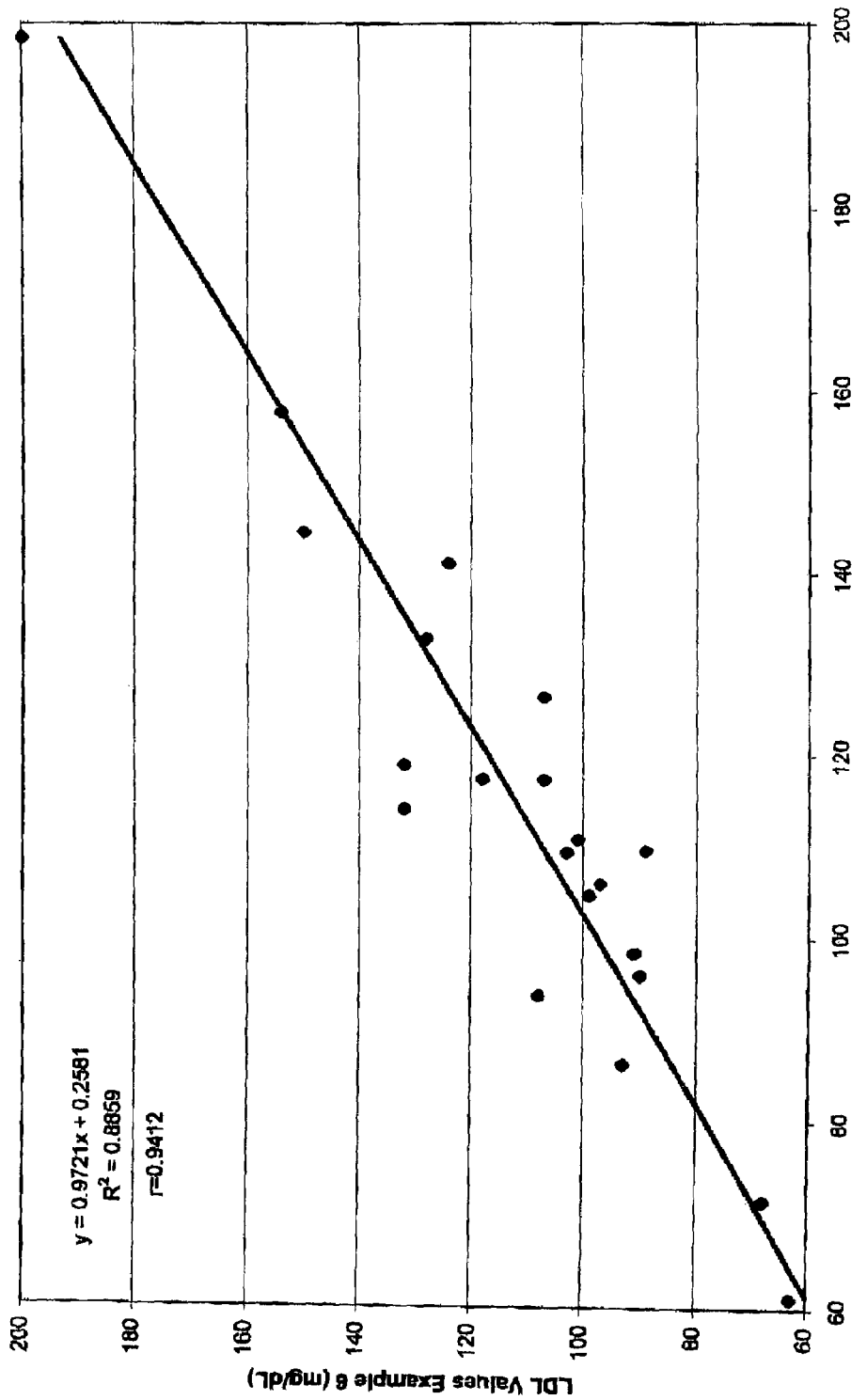

The correlation between control aliquots and fourteen assays using the test strips of Example 14 was found to be good, as shown in FIG. 8.

EXAMPLE 15

The dry strips of this example were composed of the non-glass fiber layer Accuwick Ultra (M-1), BTS SP300 (M-2), Supor 1200 (M-3), and Cholesterol Membrane (M-5). The Accuwick Ultra layer (M-1) was treated by dissolving the following chemicals into 300 g of deionized water: 6.30 g of MES buffer, 12.43 g dextran sulfate 10K, 3.08 g α-cyclodextrin sulfate, 10.04 g Sorbitol, 4.63 g sucrose, 4.37 g magnesium sulfate, 2.86 g Tetronic 304, 0.4 g of Silwet L-77, and 1.47 g of a solution containing the following: 1.03 g β-cyclodextrin polymer, 0.99 g randomly methylated β-cyclodextrin. The layer was further treated with 2.98 g of a solution containing the following: 2.99 g Emulgen 210 P, 9.00 g Pluronic L121, 1.98 g polypropylene glycol 3,500 mwt. The pH was adjusted to 6.22 using 1.75 ml of 5N NaOH. There was no treatment to the Supor 1200.

The BTS SP300 was treated with a solution resulting by dissolving the following chemicals into 300 g deionized water: 5.43 g Pluronic L121, 2.75 g magnesium sulfate, 2.39 g MOPS buffer, 2.39 g α-cyclodextrin sulfate, 1.80 g of Sorbitol, 1.82 g sucrose, 1.50 g Emulgen 210P, 0.45 g of Tetronic 304, 0.47 g Tetronic 150R1, 0.46 g Tetronic 901, 2.33 g hydroxypropyl β-cyclodextrin. the pH of the solution was 7.21 after adding ~0.9 ml of 5N NaOH.

Figure 9:
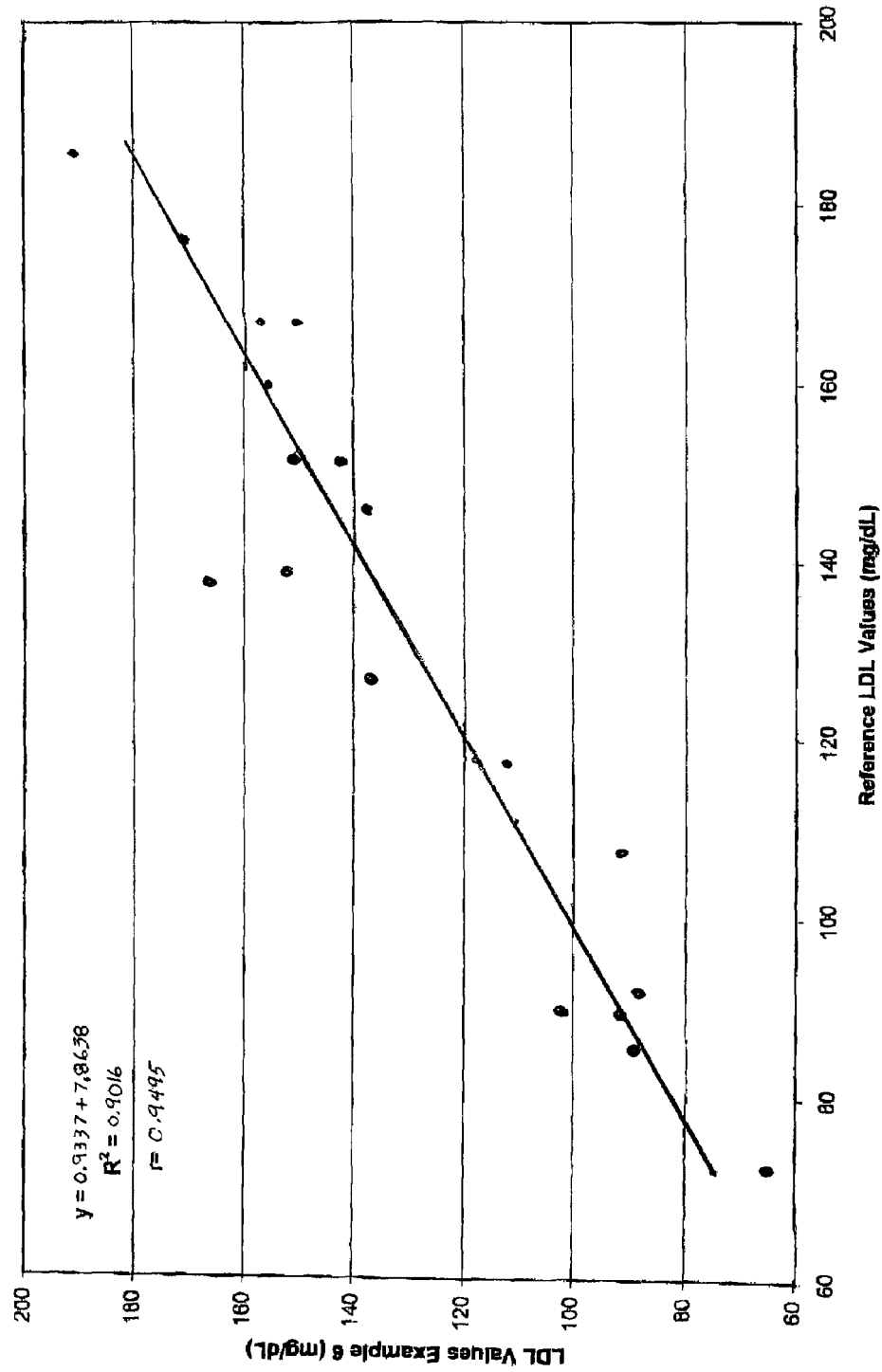

The correlation between control aliquots and fourteen assays using the test strips of Example 15 was found to be good, as shwon in FIG.9.

While the invention has been illustrated and described in detail in the drawings and foregoing description, the same should be considered as Illustrative and not restrictive in character. It is understood that only the preferred embodiments have been presented and that all changes, modifications and further applications that come within the spirit of the invention are desired to be protected.

What is claimed is:

1. A vertical flow test strip for use in the direct detection of cholesterol produced from low density lipoproteins in a whole blood, plasma or serum sample, the test strip comprising:
   a) a red blood cell blocking membrane for blocking or slowing the progress of red blood cells through the test strip;
   b) a cholesterol detection membrane for providing a color change in the presence of cholesterol; and
   c) in said test strip between said red blood cell membrane and said cholesterol detection membrane, a supply of combination of reagents that can bind with non-LDL lipoproteins to block the cholesterol in said non-LDL lipoprotiens fromb eing measured in said chloesterol detection membrane while selectively permitting low density lipoprotein cholesterol (LDL-C) to be directly measured.

2. The test strip of claim 1, wherein said combination of reagents are selected fromthe group consisting of cations, polyanions, cyclodextrin derivatives, a copolymeric surfactant and a surfactant for the coplymeric surfactant.

3. The test strip of claim 2, wherein the cations include a divalent metal.

4. The test strip of claim 3, wherein the divalent metal is magnesium.

5. The test strip of claim 2, wherein the cations include a postively charged amine effective to bind lipoproteins.

6. The test strip of claim 5, wherein the amine is triethanolamine hydrochloride.

7. The test strip of claim 2, wherein the polyanion is dextran sulfate.

8. The test strip of claim 2, wherein the cyclodextrin derivative is alpha cyclodextrin sulfate.

9. The test strip of claim 2 wherein the copolymeric surfactant is a polyoxyethylene-polyoxypropylene-polyoxyethylene hybrid, having a molecular weight range from about 2,100 to about 6,000 with a preponderance of polyoxyethylene.

10. The test strip of claim1, wherein the reagents include a high molecular wieght blocking copolymer surfactant effective to bind non-LDLs and a low molecular weight surfactant effective to increase the solubility of the blocking copolymer surfactant.

11. The test strip of claim 1, wherein said red blood cell blocking membrane is impregnated with at least some of the supply of a combination of reatgents.

12. The test strip of claim 1, further comprising at least one intermediate membrane impregnated with at least some of the supply of a combination of reagents.

13. A vertical flow test strip for use in the direct detection of cholesterol produced from low density lipoproteins in a whole blood, plasma or serum sample, the test strip comprising:

(a) a red blood cell blocking membrane for blocking or slowing the progress of red blood cells through the test strip;

(b) a cholesterol detection membrane for providing a color change in the presence of cholesterol; and (c) a supply of a combination of reagents in said test strip that block the enzymatic conversion of non-LDL lipoproteins and permitting the conversion of LDL-C lipoprotien cholesterol.

14. a test strip as in claim 13 wherein said test strip functions at room temperature.

15. A test strip as inclaim 13 wherein said combination of reagents includes block copolymer surfactants.

16. A test strip as in claim 15 wherein said combination of reagents includes lower molecular weight surfactants that increase the solubility of said block copolymer surfactants.

17. A test strip as in claim 13, further comprising triblock copolymer and surfactants inpregnated adjacent to said cholesterol detection membrane.

18. A test strip as in cliam 13, further comprising triblock copolymer and surfactants impregnated in said cholesterol detection membrane.

* * * * *